US00PP10463P

United States Patent [19]

Wain

[11] Patent Number: Plant 10,463

[45] Date of Patent: Jun. 23, 1998

[54] CHRYSANTHEMUM PLANT NAMED 'CLEAGAR GF1'

[75] Inventor: Peter Wain, Portsmouth, United Kingdom

[73] Assignee: Cleangro Limited, United Kingdom

[21] Appl. No.: 751,680

[22] Filed: Nov. 18, 1996

[51] Int. Cl.[6] ..... A01H 5/00

[52] U.S. Cl. ..... Plt./78

[58] Field of Search ..... Plt./78

[56] References Cited

U.S. PATENT DOCUMENTS

P.P. 1,166 2/1953 Boerner ..... Plt./78

P.P. 6,621 2/1989 Mack et al. ..... Plt./78

OTHER PUBLICATIONS

UPOVROM, 1997/03, Plant Variety Database, "Goldfinch" excerpt.

*Primary Examiner*—Howard J. Locker
*Attorney, Agent, or Firm*—Christie, Parker & Hale L.L.P.

[57] ABSTRACT

A distinct cultivar of Chrysanthemum plant named 'Cleagar gf1', characterized by its uniform, mounded and somewhat upright growth habit; decorative-type inflorescences; bright yellow ray florets; small, but numerous inflorescences per plant; numerous ray florets per inflorescence; and good garden performance.

2 Drawing Sheets

The present invention relates to a new and distinct cultivar of garden Chrysanthemum plant, botanically known as *Dendranthema grandiflora* and referred to by the cultivar name 'Cleagar gf1'.

The new cultivar is a product of a planned breeding program conducted by the inventor in Chichester, West Sussex, United Kingdom. The objective of the breeding program was to create new garden Chrysanthemum cultivars having desirable inflorescence colors and good garden performance.

The new cultivar originated from a cross made by the inventor of the commercial cultivar Goldmine (U.S. Plant Pat. No. 5,661) as the female, or seed, parent with the proprietary selection 10/GM/94 as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Cleager gf1'. These characteristics in combination distinguish 'Cleager gf1' as a new and distinct cultivar:

1. Uniform, mounded and somewhat upright growth habit.
2. Decorative-type inflorescences.
3. Bright yellow ray florets.
4. Small, but numerous inflorescences per plant.
5. Numerous ray florets per inflorescence.
6. Good garden performance.

The cultivar 'Cleagar gf1' has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum have a more uniform plant habit and flower more uniformly than plants of the female parent, the commercial cultivar 'Goldmine'. In addition, plants of the new Chrysanthemum have ray florets that are lighter in color than ray florets of plants of the cultivar 'Goldmine'. In the same comparisons, plants of the new Chrysanthemum are more compact and fuller and flower later than plants of the male parent, the proprietary selection 10/GM/94.

The accompanying colored photographs illustrate the overall appearance of the new cultivar, showing the colors as true as it is reasonably possible to obtain in colored reproductions of this type.

The first photograph comprises a top perspective view of a typical flowering 16.5-cm container of 'Cleagar gf1' with five cuttings in the container.

The second photograph comprises a close-up view of typical inflorescences.

Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with night temperatures ranging between 16 and 20C., day temperatures ranging between 20 and 30C., and average light levels of 5,000 to 6,000 footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar 'Cleagar gf1'.

Commerical classification: Garden Chrysanthemum.

Parentage:

*Female, or seed, parent.*—*Dendranthema grandiflora* commercial cultivar Goldmine (U.S. Plant Pat. No. 5,661).

*Male, or pollen, parent.*—*Dendranthema grandiflora* proprietary selection 10/GM/94.

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Mounded plant shape, uniform, moderately vigorous, stems somewhat upright. Freely branching.

*Plant height.*—24 to 26 cm.

*Quantity of lateral branches after removal of apical meristem.*—Usually 6 to 7.

*Foliage description.*—Number of leaves per plant: About 117. Number of leaves per lateral branch: About 18. Leaf arrangement: Alternate. Leaf size, fully expanded: Length: 5 to 5.5 cm. Width: 3.5 to 4.5 cm. Leaf apex: Mucronate. Leaf base: Truncate/attenuate. Leaf margin: Palmately lobed. Leaf texture: Leathery, smooth and fleshy. Veins prominent on abaxial surface. Abaxial and adaxial surfaces slightly pubescent. Petiole length: 2 to 2.5 cm. Color: Young foliage adaxial surface: 138A. Young foliage abaxial surface: 138B. Fully expanded foliage adaxial surface: 138A. Fully expanded foliage abaxial surface: 138B. Venation adaxial surface: 138C. Venation abaxial surface: 138D. Petiole: 138C.

Inflorescence description:

*Appearance.*—Decorative-type inflorescence form. Inflorescences borne on terminals above foliage, arising from leaf axils. Ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 49 days later. Flowers last about 4 weeks on the plant.

*Quantity of inflorescences.*—Usually 9 to 10 inflorescences per flowering stem.

*Inflorescence size.*—Diameter: About 4 cm. Depth (height): 1.5 to 2 cm.

*Opening inflorescences.*—Bud shape: Spherical. Bud size: Length: 5 to 10 mm. Width: 7.5 to 12.5 mm. Bud color: 138A/138B.

*Ray florets.*—Shape: Obovate. Size: Length: 1 to 1.5 cm. Width: 7.5 to 10 mm. Apex: Mucronate. Base: Acute. Margin: Entire. Texture: Smooth, satiny and glabrous. Number of ray florets per inflorescence: 145 to 155. Color: When opening: 12A. Mature, adaxial surface: 12B. Mature, abaxial surface: 12C. Fading to: 12C.

*Disc florets.*—None present.

*Peduncle.*—Aspect: Fairly rigid, moderate in flexibility. Length: 2.5 to 3.5 cm. Texture: Pubescent. Color: 138B.

*Sepals.—/involucral bracts* Shape: Linear. Calyx size: About 2 cm. Apex: Acute. Margin: Entire. Texture: Smooth. Quantity per inflorescence: 23 to 26. Color: Adaxial surface: 138C/138D. Abaxial surface: 138A/138B.

*Reproductive organs.*—Androecium: Not present on ray florets. Gynoecium: Style length: 2 to 4 mm. Style color: 12C. Stigma color: 12A.

Disease resistance: Under commercial greenhouse and garden conditions, plants of the new Chrysanthemum have not demonstrated resistance, tolerance nor susceptibility to diseases common to Chrysanthemums.

Seed production: Seed production has not been observed.

It is claimed:

1. A new and distinct cultivar of Chrysanthemum plant named 'Cleagar gf1', as illustrated and described.

* * * * *

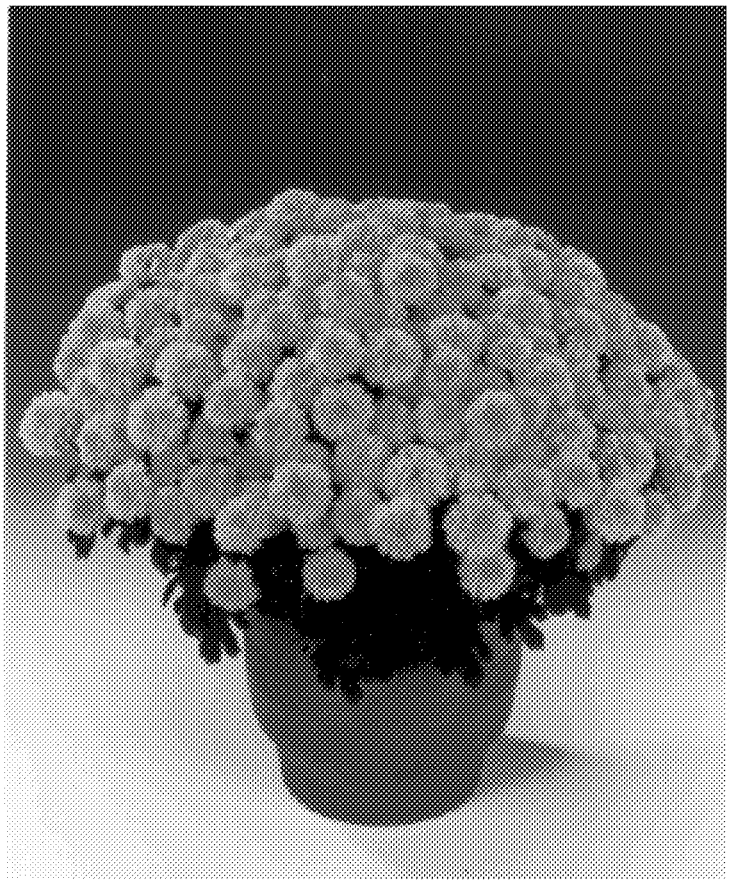

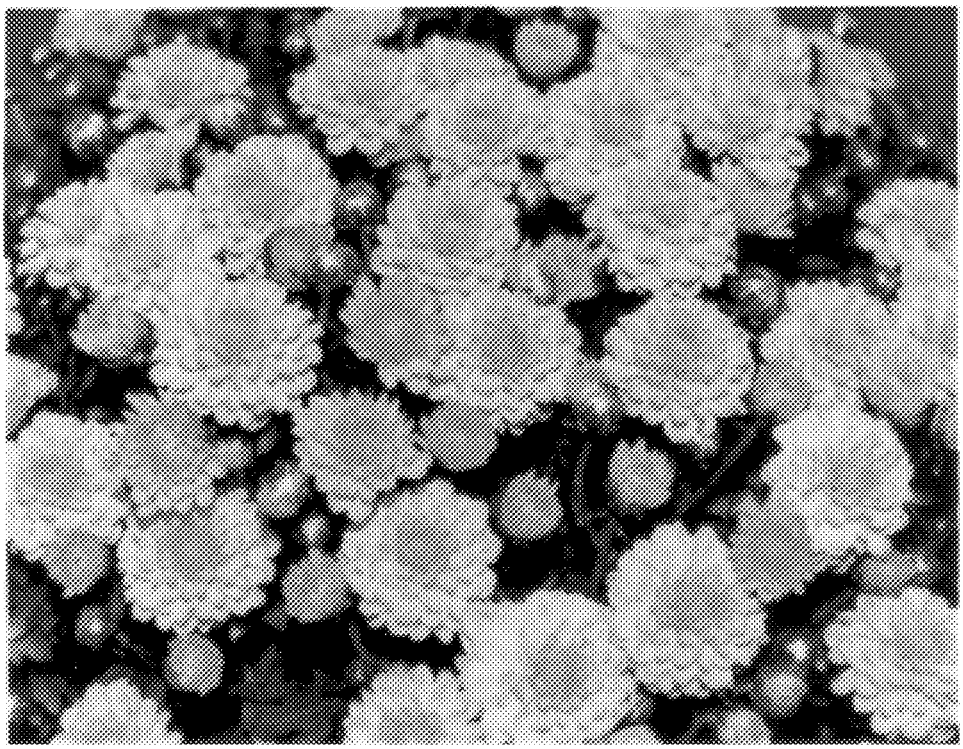

UNITED STATES PATENT AND TRADEMARK OFFICE

CERTIFICATE OF CORRECTION

PATENT NO. : Plant 10,463
DATED : June 23, 1998
INVENTOR(S) : Peter Wain

It is certified that error appears in the above-indentified patent and that said Letters Patent is hereby corrected as shown below:

Column 1, lines 25, 26, 27, change "'Cleager gf1'" to -- 'Cleagar gf1' -- (both occurrences).

Signed and Sealed this

Twentieth Day of July, 1999

*Attest:*

*Attesting Officer*

Q. TODD DICKINSON

*Acting Commissioner of Patents and Trademarks*